(12) United States Patent
Gonzalez et al.

(10) Patent No.: US 10,716,748 B2
(45) Date of Patent: Jul. 21, 2020

(54) METHOD OF TREATING HAIR (75) Inventors: Sigfredo Gonzalez, Danbury, CT (US); Anne Dussaud, Tarrytown, NY (US); JoAnne Tully, Mahopac, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 621 days.

(21) Appl. No.: 12/771,089

(22) Filed: Apr. 30, 2010

(65) Prior Publication Data
US 2011/0268681 A1   Nov. 3, 2011

(51) Int. Cl.
*A61K 8/898* (2006.01)
*A61Q 5/00* (2006.01)
*A61Q 5/12* (2006.01)
*A61Q 5/06* (2006.01)

(52) U.S. Cl.
CPC .............. *A61K 8/898* (2013.01); *A61Q 5/002* (2013.01); *A61Q 5/06* (2013.01); *A61Q 5/12* (2013.01); *A61K 2800/24* (2013.01)

(58) Field of Classification Search
None
See application file for complete search history.

(56) References Cited

U.S. PATENT DOCUMENTS

| 4,551,330 A * | 11/1985 | Wagman et al. ............... 424/59 |
| 6,251,379 B1 | 6/2001 | Omura et al. |
| 6,475,568 B1 | 11/2002 | Czech |
| 2009/0165812 A1 | 7/2009 | Resnick et al. |
| 2010/0028287 A1 | 2/2010 | Suenaga et al. |

FOREIGN PATENT DOCUMENTS

| EP | 1 837 010 A2 | 9/2007 |
| JP | 2008-143858 | 6/2008 |
| WO | 2009061360 A1 | 5/2009 |

OTHER PUBLICATIONS

How to Keep the Hair Cuticle Healthy.http://www.ehow.com/how_5547598_keep-hair-cuticle-healthy.html. Published: Oct. 29, 2010.*
INCI Directory. http://www.specialchem4cosmetics.com/services/inci/ingredient.aspx?id=16523. Published Jan. 9, 2010.*

(Continued)

*Primary Examiner* — Nicole P Babson
*Assistant Examiner* — Lori K Mattison
(74) *Attorney, Agent, or Firm* — Joseph S. Ostroff

(57) ABSTRACT

There is provided herein a method of treating thermally and/or chemically damaged including the following steps: contacting thermally and/or chemically damaged hair with a hair treating composition comprising a aminosilicone of the general formula (I):

$$MD_xD'_yM \qquad (I)$$

wherein:
$M=R^1R^2_2SiO_{1/2}$
$D=R^2_2SiO_{2/2}$, and
$D'=R^2R^3SiO_{2/2}$, and
where $R^1$ is an alkyl group having 12 to 50 carbon atoms, $R^2$ is a substituted or un-substituted hydrocarbon group having 1 to about 6 carbon atoms, $R^3$ is 3-aminopropyl group and/or a N-(2-aminoethyl)-3-aminopropyl group, x has a value of 1 to about 2,000, and y has a value of 1 to about 50.

10 Claims, 2 Drawing Sheets

(56) References Cited

OTHER PUBLICATIONS

Essential Ingredients. http://www.essentialingredients.com/productdetail.aspx?Srch=0&CatID=2&FunID=0. Published May 9, 2009.*
How to Curl Thick Hair. http://lifestyle.iloveindia.com/lounge/how-to-curl-thick-hair-2797.html. Published Dec. 1, 2009.*
Taming the Frizz Monster. http://www.curlynikki.com/2011/08/taming-frizz-monster-natural-hair-care.html. Published Aug. 25, 2011.*
Loosen Curly Hair. http://www.city-data.com/forum/hair-care/478137-loosen-curly-hair.html. Published Nov. 3, 2008.*
What is Dry Hair. http://www.sharecare.com/question/what-is-dry-hair. Published. Jun. 30, 2012.*
Virgin Brazilian hair. http://kabeilu.en.alibaba.com/product/463588208-210364380/Buy_human_hair_online_Raw_Virgin_Brazilian_hair_brand_name_hair_weave.html. Published Jan. 9, 2014.*
Divine Caroline. http://www.divinecaroline.com/beauty/hair/hair-care/how-get-super-straight-hair. Published Jan. 12, 2004.*
Where Do Human Hair Extensions Really Come From. http:www.femalefirst.co.uk/lifestyle-fashion/styletrends/extensions-5192.html. Published Jul. 22, 2008.*
How much time. http://www.dailymail.co.uk/femail/article-2250701/How-time-really-spend-doing-hair-ladies-Answer-Ten-days-year.html. Published: Dec. 19, 2012.*
Momentive: "Momentive Introduces Silsoft AX Conditioning Agent and Tospearl AQ Microspheres; Advanced Personal Care Materials", http://www.silicones.com/momentiveinternetdoc/internet/static%20files/press%20documents/2010/silsoft_ax_tospearl_aq_release-final-031010.pdf, Mar. 10, 2010 (Mar. 10, 2010).
"Momentive Introduces Silsoft AX Conditioning Agent and Tospearl AQ Microspheres; Advanced Personal Care Materials", Mar. 10, 2010 (Mar. 10, 2010), Retrieved from the Internet: URL:http://www.businesswire.com/portal/site/home/permalink/?ndmViewId=news_view&newsId=20100310005201&newsLang=en [retrieved on May 7, 2012].
Momentive:"Silsoft AX", Mar. 1, 2010 (Mar. 1, 2010), Retrieved from the Internet: URL:http://www.silicones.com/momentiveInternetDoc/Internet/Static%20Files/Documents/Marketing%20Bulletin/Silsoft%20AX%20AX%20MB%20indd.pdf [retrieved on May 8, 2012].
"Momentive Introduces Silsoft AX Conditioning Agent and Tospearl AQ Microspheres; Advanced Personal Care Materials", Focus on Surfactants, Elsevier, vol. 2010, No. 5, May 1, 2010 (May 1, 2010), pp. 3-4, XP027086198, [SSN: 1351-4210 retrieved on May 1, 2010].
Sabrina Marchioretto. Suzanne Van Doorn. Dow Corning SA. Seneffe, Belgium; Silicones Offer Multifunctional Solutions; Personal Care, Nov. 2009, pp. 21-27.
S. Ogawa et al., A curing method for permanent hair straightening using thioglycolic and dithiodiglycolic acids, J. Cosmet. Sci., 51, 379-399 (Nov./Dec. 2000).

* cited by examiner

Before iron

After iron, water only

After iron, water+ SME253

After iron, water +Silsoft Q

After iron, water+ commercial

After iron, water +EmulsionE1

METHOD OF TREATING HAIR

FIELD OF THE INVENTION

The present invention relates to a method of treating hair using a hair treating composition, specifically a silicone hair treating composition to give hair good thermal protection and lubrication properties which leave the hair shiny and feeling non-oily.

BACKGROUND OF THE INVENTION

Hair is subjected to thermal damage during hair drying, e.g., by repetitive blow dryer actions, and also during the use of an iron for curling or straightening hair. Such heat damage is enhanced in the presence of moisture and tensile stresses to cause buckling of the hair cuticles. Cuticle lifting makes the hair duller and feel less smooth.

Virgin hair surface is hydrophobic and is less prone to heat damage than bleached hair, which is usually hydrophilic. Restoration of hair hydrophobicity, which endures many wash cycles is also desirable to help protect the hair upon application of heat in the presence of moisture.

Permanent or semi permanent hair straightening and hair curling has become extremely popular. Chemicals that provide permanent hair straightening have been known for a long time: hydroxides, reducing agents such as thiols and sulfites. However, due to their strong alkalinity, these treatments tend to be harsh for the scalp and the hair.

Alternatively, effective treatments although non alkaline were often found sensitizing to the skin. Many recent developments have been aimed at finding treatments which are effective, but cause less of the aforementioned issues.

The use of oils and silicones in hair treatments has been known for a long time. Nevertheless, there still exists a need for silicones that can facilitate hair straightening or shaping processes involving the use of heat while also providing improved thermal protection.

SUMMARY OF THE INVENTION

The present invention is directed to a method for treating hair, specifically, thermally and/or chemically damaged hair, e.g., straightened or curled hair and/or bleached and/or dyed hair. The method herein provides for hair that has improved thermal properties, improved physical strength, improved hydrophobicity, less frizziness and improved shine and lubrication properties as compared to damaged hair which has not been treated by the method herein. Such improved properties exist prior to and after subsequent heat treatment of the treated hair.

In one embodiment herein there is provided a method of treating thermally and/or chemically damaged hair comprising:

contacting thermally and/or chemically damaged hair with a hair treating composition comprising a aminosilicone of the general formula (I):

$$MD_xD'_yM \quad (I)$$

wherein:
$M=R^1R^2_2SiO_{1/2}$
$D=R^2_2SiO_{2/2}$, and
$D'=R^2R^3SiO_{2/2}$, and
where $R^1$ is an alkyl group having 12 to about 50 carbon atoms, $R^2$ is a substituted or un-substituted hydrocarbon group having 1 to about 6 carbon atoms, $R^3$ is 3-aminopropyl group and/or a N-(2-aminoethyl)-3-aminopropyl group, x has a value of 1 to about 2,000, and y has a value of 1 to about 50.

Namely, the hair treating composition of the present invention is characterized by containing a both terminally long-chain alkylamino group-modified polyorganosiloxane having a viscosity at 25° C. of about 1,000 to about 5,000,000 mPas, represented by the formula (I) above.

DETAILED DESCRIPTION OF THE INVENTION

Thermally and/or chemically damaged hair can comprise hair that has been subjected to at least one of bleaching, dying, wetting by water, hair straightening such as hair straightening with an iron, hair shaping, repeated blow-drying, e.g., blow-drying for more than 15 minutes at more than three non-immediately successive instances in a 24 hour period, hair permanent treatment, and semi-permanent hair treatment, and the like, prior to treatment with the hair treating composition. Bleaching can have been done by any known means such as the use of one or more of hydrogen peroxide, sodium hydroxide and the like.

Thermally and/or chemically damaged hair can comprise a level of damage that is undesirable from a cosmetic standpoint, in that such damaged hair can contain cuticle lifting, decreased hydrophobicity and the like, wherein hair is rendered with one or more of visible frizziness, flatness, lack of shine and/or lubricity, coarseness, a heavy feel, physical knotting and a generally undesirable feel to the touch.

Specifically, such damaged hair can have a low level of thermal protection, i.e. following the application of heat to such damaged hair, the damaged hair can have an increased level of frizziness and/or cuticle lifting and/or cuticle damage.

Specifically, in another embodiment, such damaged hair can have a high volume factor prior to treatment with the hair treating composition. Volume factor can be determined by different methods known to those skilled in the art, such as the non-limiting example of a ratio of the measured maximum width in the hair tip region (Lt) to the measured maximum width at the root end (Lr)((Lt)/(Lr)). Such a measurement can be conducted with a ruler. A method for conducting such a determination of volume factor is described in WO 2009/061360 the contents of which are incorporated herein by reference. In one non-limiting embodiment, such a determination of volume factor is made following contacting of the thermally and/or chemically damaged hair with the hair treating composition described herein, followed by removal of excess water and the ironing of the hair at medium heat in a Revlon flat iron for seven minutes.

Thermally and/or chemically damaged hair used in the method herein prior to treatment with the hair treating composition can have a (Lt)/(Lr) ratio of greater than about 3.7, preferably greater than about 4.0, with upper limits to such a range not being fixed although such upper limits could constitute values of any one of 5, 6, 7, 8, 9 or 10 or greater, with such values determined following the above described Revlon iron treatment wherein the hair sample was not treated with a hair treating composition of the invention or was treated with a composition other than the hair treating composition of the invention.

Further, such thermally and/or chemically damaged hair used in the method herein can have decreased strength (prior to treatment with the hair treating composition), e.g., decreased tensile strength, as compared to virgin hair, i.e., hair that has not been thermally and/or chemically damaged. In one non-limiting embodiment herein the thermally and/or chemically damaged hair used in the method herein prior to treatment with the hair treating composition has a break strength of less than about 0.0146 gmf/sq. microns, preferably less than about 0.0140 gmf/sq. microns and most preferably less than about 0.0135 gmf/sq. microns.

In one other embodiment herein the chemically and/or thermally damaged hair used in the in the method herein has a decreased hydrophobicity as compared to virgin hair. In one non-limiting embodiment the chemically and/or thermally damaged hair used in the in the method herein has a hydrophobicity prior to treatment with the hair treating composition of less than 200 seconds under an adapted AATCC Test Method 79-1992. Such an adapted AATCC Test Method 79-1992 is conducted by holding a hair sample which has been washed once, five times or 10 times with a 10 weight percent sodium lauryl ether sulfate (SLES) solution, taut in a hair holder, followed by applying a drop of deionized water onto the taut hair sample surface via a dropper. Time is measured from the time of application of the drop of water until the drop of water completely penetrates the hair sample and is reported in seconds. In one embodiment herein the chemically and/or thermally damaged hair used in the method herein has a hydrophobicity prior to treatment with the hair treating composition of less than 200 seconds, preferably less than 150 seconds, more preferably less than 100 seconds and most preferably less than 50 seconds, e.g., less than 10 seconds.

In one embodiment the chemically and/or thermally damaged hair used in the method herein prior to treatment with the hair treating composition can have one or more of a measured maximum width in the hair tip region (Lt) to the measured maximum width at the root end (Lr) ratio ((Lt)/(Lr)) of greater than about 3.7, a break strength of less than about 0.0146 gmf/sq. microns and a hydrophobicity of less than 200 seconds under an adapted AATCC Test Method 79-1992.

Preferably, the means of contacting the thermally and/or chemically damaged hair with a hair treating composition can comprise any known method such as dipping, soaking, shampooing, washing, spraying, rubbing and the like. The hair treating composition can also be applied using implements or devices. For example useful implements can be non-woven clothes, sponges, brushes or delivery device mounted on the hot iron.

In one embodiment herein the hair treating composition is an aqueous composition or a non-aqueous composition. Preferably, the hair treating composition is an oil-in-water emulsion. In one other embodiment, the hair treating composition is a water-in-oil emulsion.

Embodiments of a hair treating composition according to the present invention are described as follows. A hair treating composition according to an embodiment of the present invention contains an aminosilicone represented by the formula (I) above.

In aminosilicone formula (I) $R^1$ is an alkyl group having 12 to about 50 carbon atoms, and may be linear or branched. Preferably, $R^1$ is a linear or branched alkyl group having 14 to about 50 carbon atoms, and more preferably 16 to about 50 carbon atoms. In one embodiment $R^1$ is a linear or branched alkyl group of from about 15 to about 20 carbon atoms. In one other embodiment, $R^1$ is a linear or branched alkyl group of from about 30 to about 45 carbon atoms.

In aminosilicone (I) $R^2$ is a substituted or un-substituted hydrocarbon group having 1 to 6 carbon atoms. Examples of the un-substituted hydrocarbon groups are, for instance, linear or branched alkyl groups such as methyl, ethyl, butyl or hexyl; cycloalkyl groups such as cyclohexyl; alkoxy groups such as methoxy, ethoxy, propoxy or butoxy; aryl groups such as phenyl, tryl or naphtyl; aralkyl groups such as benzyl, β-phenylethyl or methylbenzyl; alkenyl groups such as vinyl or allyl, and the like. Examples of the substituted alkyl groups are, for instance, fluoroalkyl groups such as 3,3,3-trifluoropropyl, and the like. Among them, preferable is an alkyl group or an aryl group, especially preferable is methyl or phenyl.

In aminosilicone (I) $R^3$ is 3-aminopropyl group and/or N-(2-aminoethyl)-3-aminopropyl group.

In one specific embodiment, $R^1$ is an alkyl group containing from about 15 to about 20 carbon atoms, $R^2$ is methyl and $R^3$ is N-(2-aminoethyl)-3-aminopropyl group.

In another specific embodiment, $R^1$ is an alkyl group containing from about 30 to about 45 carbon atoms, $R^2$ is methyl and $R^3$ is N-(2-aminoethyl)-3-aminopropyl group.

In aminosilicone formula (I) which represents the both terminally long-chain alkylamino group-modified polyorganosiloxane used in the present invention, a value of x is within the range of 1 to about 2,000, preferably within the range of about 10 to about 1,500, more preferably from about 50 to about 1500, even more preferably from about 100 to about 1250 and most preferably from about 500 to about 1,000. When the value of x is less than 1 and is more than 2,000, the resulting hair treating composition is inferior in smoothness (sliding smoothness), and, in each case, have insufficient effect. In aminosilicone (I) a value of y is within the range of 1 to about 50, particularly preferable y is within the range of 2 to about 40. When the value of y is less than 1, adsorption to hair is lower, and when more than 50, the feeling of sliding smoothness to dry hair becomes relatively heavy.

It is necessary that at 25° C., a viscosity of the aminosilicone (I) of the present invention is about 1,000 to about 5,000,000 mPas, preferably about 2,000 to about 4,000,000 mPas. When the viscosity is less than 1,000 mPas, the feeling of sliding smoothness of hair becomes relatively heavy, and when more than about 5,000,000 mPas, the both terminally long-chain alkylamino group-modified polyorganosiloxane is hard to spread on the surface of hair uniformly. As a result, the feeling of sliding smoothness becomes also heavy in this case, and thus the feeling of light sliding smoothness which is the effect of the present invention is hard to be obtained.

A nitrogen content of the aminosilicone (I) is preferably 0.01 to about 0.3% by weight, and is particularly preferably 0.05 to about 0.25% by weight. When the nitrogen content is less than about 0.01% by weight, adsorption to hair is lower, and when more than about 0.3% by weight, the feeling of sliding smoothness to dry hair becomes relatively heavy.

Similarly, according to the method of the present invention, it is preferable that the hair be contacted with the aminosilicone (I) to achieve a silicone concentration on the hair of from about 0.01 to about 0.5% by weight, preferably from about 0.05 to about 0.3% by weight.

In the hair treating composition of the present invention, when other silicone compounds are used at the same time, it is possible to meet requirements to afford more sensitive touch. When used together with other silicones, it is desirable to previously blend the silicones with each other, and then to use the blended product in the form of an emulsion. Further, the hair treating composition comprising the aminosilicone (I) is preferably blended in the form of an emulsion.

Co-usable silicones include polydimethylsiloxane(dimethicone), cyclic polydimethylsiloxane(cyclomethicone), and the like. As the polydimethylsiloxane, at 25° C., those having a wide range of viscosity of 0.05 to 20,000 Pas·s can be used. Through blending, it is possible to adjust smoothness particularly to dry hair. On the other hand, the cyclic polydimethylsiloxane can adjust smoothness particularly to wet hair.

When the hair treatment composition is a water type such as shampoo or rinse, it is preferable that the aminosilicone (I), or the blended product of the aminosilicone (I) and the above-mentioned other silicones is previously emulsified to be an emulsion, and then blended.

By constituting in this way, the particle size of the silicone particles distributed in the hair treatment composition can be controlled easily, and the adjustment of feeling given becomes easy. Namely, an emulsion containing the silicone particles having large particle sizes is suitable to a rinse and a conditioner which are hair treatment compositions which are washed out after being applied, since the silicone portion easily remains on the hair. However, when the particle size is too large, there is a problem in that the stability in the hair treatment composition becomes lowered. Therefore, the optimal particle size of the silicone particles is different depending on the type of respective hair treatment composition, and thus, it is necessary to control the particle size.

In the present invention, as a preparation method of the emulsion containing the aminosilicone (I), a publicly known method can be employed. For example, there are non-limiting emulsifying methods by using an emulsion machine such as a colloid mill, a line mixer, a homomixer, a homogenizer, or an integrated emulsion machine having an anchor mixer and homomixer, or an anchor mixer and disper mixer.

In the preparation of the emulsion, a surfactant and water are used. As the surfactant, any of an anionic surfactant, a cationic surfactant, a nonionic surfactant and an amphoteric surfactant may be used, and they may be used alone or as a mixture of two or more.

As the anionic surfactant, there are exemplified dodecylbenzenesulfonic acid, octylbenzenesulfonic acid, polyoxyethylene lauryl sulfate, lauryl sulfate, tetradecenesulfonic acid, hydroxytetradecenesulfonic acid, and sodium salt, potassium salt, triethanolamine salt thereof, and the like.

As the cationic surfactant, there are exemplified laurylrimethylanunonium hydroxide, stearyltrimethylammonium hydroxide, dioctyldimethylammonium hydroxide, distearyldimethylammonium hydroxide, lauryltrimethylammonium chloride, stearyltrimethylammonium chloride, cetyltrimethylammonium chloride, dicocyldimethylammonium chloride, distearyldimethylammonium chloride, benzalkonium chloride, stearyldimethylbenzylammonium chloride, and the like. Suitable cationic surfactants are also amidoamine derivatives such as behenamidopropyl dimethylamine or esterquat based on long alkyl chain, for example behenoyl PG-trimonium chloride.

As the nonionic surfactant, there are exemplified polyoxyethylene lauryl ether, polyoxyethylene fatty acid ester, polyoxyethylene sorbitan fatty acid ester, sorbitan fatty acid ester, glycerine fatty acid ester, polyoxyethylene hardened castor oil, polyoxyethylene sorbitol fatty acid ester, and the like. Other suitable nonionic are alkylpolyglucosides As the amphoteric surfactant, there are exemplified laurylamine oxide, lauryl betaine, cocamidopropyl betaine, and the like.

The type of surfactant is selected depending on compatibility with other components in the hair treatment composition. For example, when the target hair treatment composition is an anionic composition such as a shampoo, at least one surfactant selected from the anionic surfactant, the amphoteric surfactant and the nonionic surfactant is used preferably, and when the target hair treatment composition is a cationic composition such as a rinse, a conditioner or the like, at least one surfactant selected from the cationic surfactant, the amphoteric surfactant and the nonionic surfactant is used preferably. Particularly the nonionic surfactant is used preferably, since particle sizes of the emulsion can be controlled relatively easily, and blending with both the anionic composition and the cationic composition can be stably done.

Here, examples of the nonionic surfactants are polyoxyethylene (6) lauryl ether, polyoxyethylene (7) cetyl ether, polyoxyethylene (20) stearyl ether, polyoxyethylene (3) octylphenyl ether, polyoxyethylene (18) nonylphenyl ether, polyethylene glycol monostearate (EO14), polyethylene glycol distearate (EO80), polyoxyethylene (20) sorbitan, polyoxyethylene (20) hardened castor oil, polyoxyethylene (20) sorbitan monolaurate, polyoxyethylene (20) sorbitan monopalmitate, polyoxyethylene (6) sorbitan monostearate, polyoxyethylene (20) sorbitan trioleate, polyoxyethylene (40) sorbit tetraoleate, polyoxyethylene (15) glyceryl monooleate, polyoxyethylene (15) glyceryl monostearate, sorbitan monopalmitate, polyoxyethylene (10) behenyl ether, polyoxyethylene (10) phytosterol, polyoxyethylene (10) polyoxypropylene (4) cetyl ether, polyoxyethylene (5) stearylamine, polyoxyethylene (8) stearylpropylenediamine, polyoxyethylene (5) cetyl ether sodium phosphate, and the like. Among those nonionic surfactants, one having a HLB value of 6 to 20 is preferably used together, since the stability of resulting emulsion is good.

A blending amount of the surfactant is preferably within the range of 1 to about 40% by weight of the whole emulsion, more preferably 2 to about 20% by weight. When less than about 1% by weight, it is difficult to disperse each component well, and when more than about 40% by weight, the stability of the emulsion becomes lowered. A blending amount of water as a dispersing medium is preferably within the range of about 20 to about 90% by weight of the whole emulsion, more preferably about 30 to about 80% by weight.

At the time of emulsification, by neutralizing the amino portion with an acid, the stability of the emulsion can be improved. The acids used at that time include organic acids such as acetic acid or lactic acid, and inorganic acids such as hydrochloric acid, sulfuric acid or phosphoric acid.

Examples of the hair treating composition according to the present invention include at least one hair cosmetic such as the non-limiting examples of a shampoo, a rinse, a conditioner, a treatment, a hair styling product, a hair mousse, a hair cream, a gel, and the like. The individual hair treatment compositions have different purposes but have the common characteristics of providing the hair with smooth touch.

When the emulsion containing the aminosilicone (I) according to the present invention is used as a rinse effective agent and a conditioner, it is desirable to blend one, two or more of the quaternary ammonium salts in an amount of 0.1 to about 5% by weight to the whole hair treatment composition. When the quaternary ammonium salt is less than 0.1% by weight, rinsing effect is not enough, and when more than about 5% by weight, a viscosity of resulting hair treatment composition becomes so high that it is hard to use it.

Examples of the quaternary ammonium salts include cetyltrimethylammonium chloride, stearyltrimethylammonium chloride, behenyltrimethylammonium chloride, behenyldimethylhydroxycetylammonium chloride, stearyldimethylammonium chloride, cetyltriethylammonium methyl sulfate, and the like. Among them, stearyltrimethylammonium chloride, behenyltrimethylammonium chloride and stearyldimethylbenzylammonium chloride are particularly preferable. Suitable cationic surfactants are also amidoamine derivatives such as behenamidopropyl dimethylamine or esterquat based on long alkyl chain, for example behenoyl PG-trimonium chloride.

When using the emulsion comprising the aminosilicone (I) of the present invention as a detergent such as shampoo, anionic surfactants such as fatty acid soap, α-acylsulfonate, alkylsulfonate, alkylnaphthalenesulfonate, alkylsulfate, polyoxyethylene alkyl ether sulfate, alkylamide sulfate, alkylphosphate, alkylamidephosphate, alkyloyl alkyl taurate or N-acylamino acid salt; nonionic surfactants, for example, glycerine fatty acid esters such as glyceryl monostearate and glyceryl monooleate, sorbitan fatty acid esters such as sorbitan stearate or sorbitan oleate, polyoxyethylene sorbitan fatty acid esters such as polyoxyethylene sorbitan palm oil fatty acid ester, polyoxyethylene sorbitan monopalmitate or plyoxyethylene sorbitane monostearate, polyoxyethylene alkyl ethers such as polyoxyethylene laurylether or polyoxyethylene stearyl ether, polyethylene glycol fatty acid esters such as polyethylene glycol monolaurate, polyethylene glycol distearate or glycol distearate, and alkylalkanol amide such as lauric acid diethanolamide or palm oil fatty acid diethanolamide; and anphoteric surfactants, for example, betaines such as lauryl dimethylaminoacetic acid betaine, stearyl dimethylaminoacetic acid betaine, 2-alkyl-N-carboxymethyl-N-hydroxyethylimidazolinium betaine, palm oil fatty acid amidopropyl betaine or lauric acid amidopropyl betaine, aminocarboxylate, and imidazoline derivative. It is desirable that one, two or more of the surfactants are added to the hair treatment composition in an amount of about 5 to about 40% by weight. When less than 5% by weight, detergency and foaming property are lowered, and when more than 40% by weight, a viscosity of resulting hair treatment composition becomes so high that it is hard to use it.

In the hair treatment composition of the present invention, other than the aforementioned components, there may be blended, depending on the intended use, oil components such as liquid paraffin, squalane, lanolin derivative, higher alcohol or various ester oil, water soluble oil components such as ethylene glycol, propylene glycol, glycerin or sorbitol polyethylene glycol, moisturizers such as the non-limiting example of pyrrolidone carboxylic acid, thickeners such as carboxyvinyl polymer, cationic polymers such as cation-modified cellulose ether derivative, polyvinylpyrrolidone derivative quaternary ammonium salt, diaryl dimethylammonium chloride, polyamide derivative quaternary ammonium salt, polyoxyethylene polyalkylene or polyamine, ultraviolet ray absorbents, perfumes, and the like.

In one embodiment herein the method herein can further comprise rinsing the chemically and/or thermally damaged hair that has been treated with the hair treating composition, prior to and/or after any optional subsequent heat treatment and/or chemical treatment, such as the non-limiting example of rinsing out shampoo or conditioner that comprises the hair treating composition. In another embodiment herein, the method further comprises not rinsing the hair treating composition from the chemically and/or thermally damaged hair that has been treated with the hair treating composition, prior to and/or after any optional subsequent heat treatment and/or chemical treatment, such as the non-limiting example of the use of hair spray, hair gel or the like which comprises the hair treatment composition.

In one embodiment herein the above described method of treating thermally and/or chemically damaged hair can further comprise applying heat for physically smoothing and/or shaping the treated hair. Such application of heat for physically smoothing and/or shaping the treated hair can comprise the use of at least one heat applying device selected from the group consisting of a straightening iron, a curling iron, a blow dryer, and a heating bonnet. Such application of heat for physically smoothing and/or shaping the treated hair can occur during and/or after contacting the chemically and/or thermally damaged hair with the hair treating composition. A heat-applying device is any device that can provide sufficient heat to hair being treated therewith to provide for a desired level of physical smoothing and/or shaping, e.g., straightening or curling. Methods for using such devices and the use of such devices to apply heat to hair for physically smoothing and/or shaping hair are well known by those skilled in the art and will not be described herein. In one embodiment, the heat applying device used in the method herein can be used in conjunction with at least one of a comb, brush, hair pin, hair clip, head band, and hair band, and the like.

There is also provided herein hair that has been treated by the method described herein wherein the treated hair has at least one of greater thermal protection, greater hydrophobicity, lower frizziness, greater break strength, and improved shine than equivalent hair that has not been treated by the hair treatment composition. Such improved properties that are present in the hair treated by the method described herein, are present both before, and after, any subsequent beat treatment of the hair treated with the hair treating composition of the method herein. Such subsequent heat treatment can comprise the use of any of the above-described heat applying devices and/or methods described herein.

Such greater hydrophobicity of hair that has been treated by the method herein is greater than about 200 seconds under the above described adapted AATCC Test Method, preferably greater than about 250 seconds, more preferably greater than about 300 seconds, even more preferably greater than about 400 seconds, and most preferably greater than about 500 seconds, each following at least one wash in said AATCC Test Method.

Such lower friziness comprises a (Lt)/(Lr) ratio of less than about 3.6, preferably less than about 3.5 and most preferably less than about 3.0 following treatment of the hair sample according to the method described herein and the use of the subsequent Revlon iron treatment described above.

Such greater break strength of hair that been treated by treated by the method herein is greater than about 0.0147 gmf/sq. micron, preferably greater than about 0.0148 gmf/sq. micron, and most preferably greater than about 0.0150 gmf/sq. micron.

EXAMPLES

Emulsion of Aminosilicone 1 (E1)

The aminosilicone modified at both ends was represented by formula I, where x=650, y=3.5 and $R^1$ is an alkyl group having 16 to 18 carbon atoms, $R^2$ is a methyl group and $R^3$ is N-(2-aminoethyl)-3-aminopropyl group.

This aminosilicone was emulsified with a nonionic surfactant Tergitol TMN-6 available from Dow.

A 100 g of emulsion was prepared according to the following protocol. 20 g of the aminosilicone and 12 g of Tergitol TMN-6 were mixed in a flask with high shear blade at 800 rpm while heating mixture to 65° C. After a homogeneous blend was obtained, 10 g of dionized water was slowly added under shear. Acetic acid was added slowly. The remaining water was added at once while mixing with high shear. The flask was removed from heat and the emulsion was mixed by shear for another 30 min. A clear microemulsion was obtained.

Emulsion of Aminosilicone 2 (E2)

The aminosilicone modified at both ends was represented by formula I, where x=650, y=3.5 and $R^1$ is an alkyl group having 30 to 45 carbon atoms, $R^2$ is a methyl group and $R^3$ is N-(2-aminoethyl)-3-aminopropyl group.

This aminosilicone was emulsified with a nonionic surfactant Tergitol TMN-6. A 100 g of emulsion was prepared according to the following protocol. 20 g of the aminosilicone and 12 g of Tergitol TMN-6 were mixed in a flask with high shear blade at 800 rpm while heating mixture to 65° C. After a homogeneous blend was obtained, 10 g of dionized water was slowly added under shear. Acetic acid was added slowly. The remaining water was added at once while mixing with high shear. The flask was removed from heat and the emulsion was mixed by shear for another 30 min. A whitish minimulsion was obtained.

Damp Iron Test to Assess Thermal Protection

Figure 1:
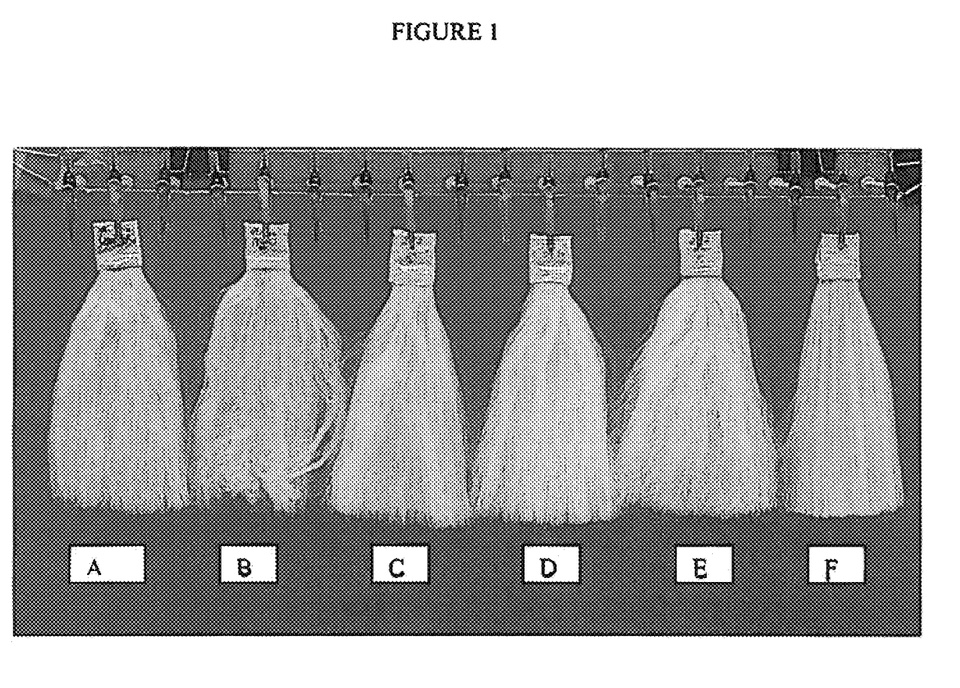
FIG. 1 shows the damp ironing result on damaged hair tresses which have been treated with comparative formulations and formulations of the invention.

Alkylaminosilicone containing treatment and comparative treatments are shown in Table 1. Double-bleached 4 g tresses (15 cm long) obtained from Hair International were used. The tresses were treated with a 0.5% NaOH solution for 2 minutes at room temperature in order to induce a very visible frizziness. The tresses were then washed 2 times with a 10% sodium lauryl ether sulfate (SLES) solution, blow-dried, disentangled with a comb. The test tress was dipped in the dispersion described in Table 1 for 60 seconds. Excess water was removed by squeezing the wet tress between the index and middle finger. The damp tress was then ironed at medium heat, in a Revlon flat iron for 7 minutes. After 7 minutes, the tress was dry to the touch. FIG. 1 shows the results of this experiment after the ironing step for each tress A-F. Clearly the water-treated tress showed visible severe damage in that the hair strand had knotted and felt very coarse. The alkylaminosilicone treated tress provides significant thermal protection compared to all the other treatments and allowed the removal of initial tress frizzyness without visible severe damage. In addition, the alkylaminosilicone treated tress was shinier than the other tresses.

TABLE 1

Hair treatment for damp iron

| Tress | | |
|---|---|---|
| A | Comparative 1 | Before iron |
| B | Comparative 2 | Damp iron with DI water |
| C | Comparative 3 | Damp iron with 1% aminosilicone SME253 |
| D | Comparative 4 | Damp iron with 1% quaternized silicone Silsoft Q |
| E | Comparative 5 | Damp iron with leave-in conditioner |
| F | Example | Damp iron with 1% alkylaminosilicone from emulsion E1 |

Aminosilicone and quaternized silicone in comparative 2 and 3 are from the emulsion Silsoft* SME253 and Silsoft Q are conventional silicones available from Momentive Performance Materials Inc. The leave-in conditioner (comparative 5) is the leave-in strengthener from SoftSheen Carson Optimum Care relaxing kit. Tresses C-F additionally contain water.

Assessment of Frizziness Removal

As in the previous experiment, 15 cm long double-bleached 4 g tresses from Hair International were used. The hair frizzyness induced by the harsh base treatment (0.5% NaOH) described earlier manifests itself by a significant increase of the tress volume. The volume increase of the tress was evaluated by measuring the maximum width (Lt) of the tress in the hair tip region and the width of the tress at the root end (Lr) with a ruler. This test is described in WO 2009/061360 A1 and is incorporated herein by reference. The tress is disentangled before the ironing step. After immersion in the aqueous treatment, the tress is ironed as described earlier. After ironing, the tresses are hung and length at the root and at the tip are measured. A volume factor was defined by the ratio Lt/Lr. The hair tress is considered very straight and not frizzy if Lt/Lr is less or equal to 2.6, as shown by the virgin untreated straight tress (comparative). Volume ratio much higher than 4 indicates very high level of frizzyness and high damage. The volume factor measured before and after ironing, for each treatment is displayed in Table 2. The experiment has been performed in duplicate. The data show that the aminosilicone modified at the end by long alkyl chain treatment (emulsion E1 and emulsion E2) during ironing allowed a significant removal of frizzyness, superior to the conventional aminosilicone treatment.

TABLE 2

| | | volume factor | |
|---|---|---|---|
| | Damp iron Treatment | before iron | after iron |
| Tress B (comparative) | Tap water | 4.5 | 4.5 |
| Tress C (comparative) | 1% aminosilicone SME253 | 4.5 | 4.5 |
| Tress D (comparative) | 1% quaternized silicone Silsoft Q | 4.5 | 4.5 |
| Tress E (comparative) | Leave-in conditioner | 4.5 | 5.3 |
| Tress F (example) | 1% alkylaminosilicone from emulsion E1 | 4.5 | 3.5 |
| Tress G | 1% alkylaminosilicone from emulsion E2 | 4.5 | 3 |
| Tress H (comparative) | Straight Virgin hair, no treatment | 2.6 | 2.6 |

Comparative tress H is the virgin untreated straight hair. The aminosilicone in comparative tress D is prepared with Silsoft SME253 from Momentive Performance Materials Inc.

Thermal Protection Assessment by Scanning Electron Microscopy (SEM)

A Scanning Electron Microscopy assesses the damage. The microscope was a FEI Quanta 200 Scanning Electron Microscope and the sputter coater was from Emitech. The test conditions were High vacuum (~3×10$^{-1}$ Pa), 20 kV Voltage, Spot Size 3.0, WD~40 mm. Each hair samples were cut into small pieces (~1-1.5 cm length), and five of them were randomly selected for gold coating (25 mA, 4 minutes) followed by SEM observation.

Figure 2:
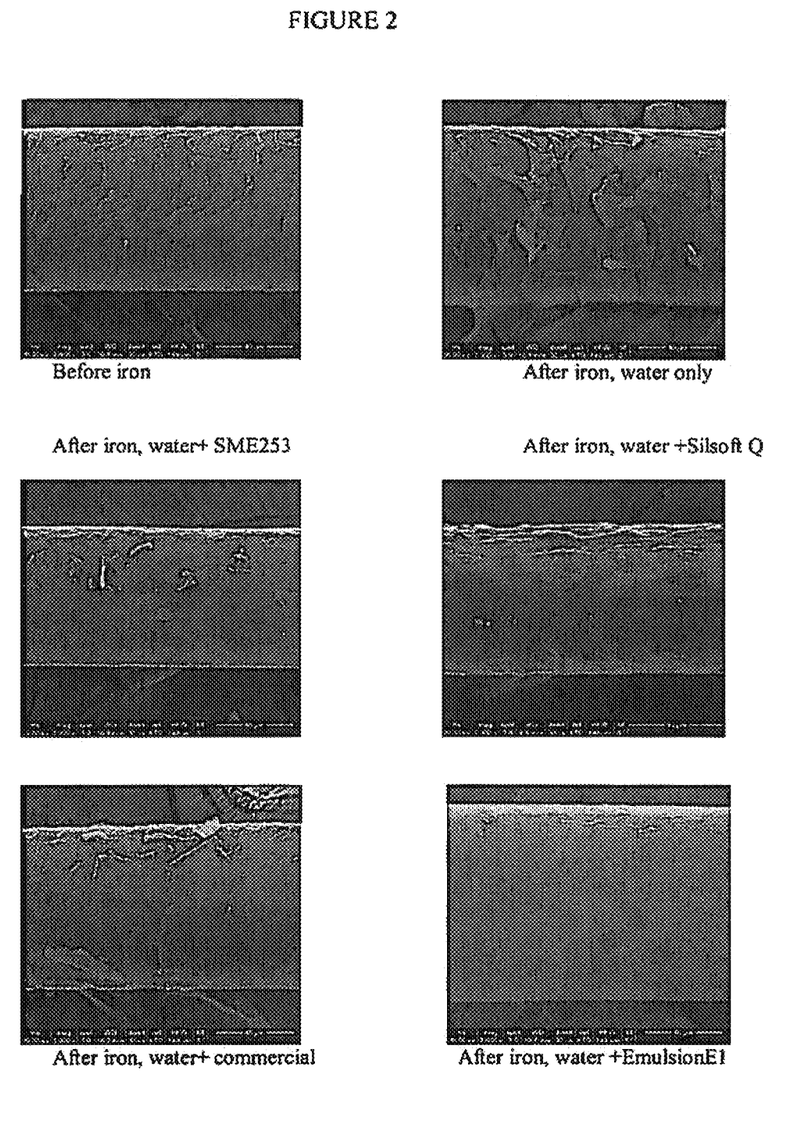
FIG. 2 shows Scanning Electron Microscopy pictures from fibers which have been treated with comparative formulations and formulations of the invention

Typical SEM pictures of fibers from samples A-F (table 1) are shown in FIG. 2. Sample A showed the un-lifted hair cuticles of the hair before iron. The sample B treated with heat and no silicone treatments showed severe cuticle lifting. Sample C treated with aminosilicones SME253 showed less cuticle lifting. Sample D showed less cuticle lifting, but a non-uniform coating. Sample E treated with the commercial products showed significant cuticle damage. In contrast, sample F showed a continuous coating films preventing cuticle lifting.

Thermal Protection Assessment Using Tensile Test:

Heat damage was assessed by single fiber tensile test, using a Diastron tensile tester with a automated 100 fibers cassette. 50 fibers were taken from the tresses A, B, C, F described in table 1. Averaged break strength (N=50) is the stress at break and is shown in Table 4. Data showed that damp heat treatment without silicone significantly reduces break strength compare to the break strength before iron. Treatment with aminosilicone SME253 (C) does not reduce the percentage of premature break and does not prevent the break strength loss. In contrast, treatment with aminosilicone E1 reduces the break strength loss and the percentage of premature break. Consistently to the observations shown before, the tensile test showed that the treatment with aminosilicone E1 reduces heat damage.

TABLE 4

|  | Break strength (gmf/sq. micron) | % of premature break* |
|---|---|---|
| Initial (A) | 0.0158 | 8 |
| Heat + water (B) | 0.0139 | 17 |
| Heat + water + SME253 (C) | 0.0142 | 18 |
| Heat + water + Emulsion E1 (F) | 0.0148 | 6 |

*premature break which occurs at less than 15% extension

Durable Hydrophobization of Hair

Single bleached hair was treated once with a silicone treatment by the immersion method described earlier and hydrophobicity was assessed after 1 wash, 5 washes, and 10 washes, where the wash was performed with a 10% SLES solution. Results were also compared with a tress that was not treated with silicone. Long single-bleached tresses from Hair International Samples were treated with silicone emulsions by the immersion method described earlier. Silicone treatments are summarized in Table 5. Each tress was dipped into 100 ml of the dilute silicone dispersion (0.3% active) for 60 s, excess liquid was squeezed out and tress was blown dry. The tress was kept overnight at room temperature before the shampooing step. The tress was then shampooed with a 10% SLES solution (0.25 ml/g hair), rinsed for 30 s in lukewarm tap water and blown dried.

The hydrophobicity of the hair tress was evaluated by measuring the time required for a drop of water to penetrate the surface of the hair tress secured horizontally with clamps according to a method adapted from the AATCC Test Method 79-1992 for textile samples. The hair tress is held taut into the hair holder. A drop of deionized water was applied onto the tress surface via a dropper and a timer was started. The timer was stopped when the drop of water completely penetrated the tress and was recorded in seconds. The value reported is the average of 5-drop tests readings, shown in the table 3. The test was terminated at 300 seconds. A value of 300 seconds indicates that the drop did not penetrate the hair tress within the 5 min observation time.

Data showed that emulsion E1 provide a durable hydrophobic finish enduring at least 10 washes.

TABLE 5

|  |  | Active concentration | Wicking (second) | | |
|---|---|---|---|---|---|
|  |  |  | Initial treatment | 1 wash | 5 washes | 10 washes |
| Comparative 1 | No silicone | 0 | | <10 | <10 | <10 |
| Comparative 2 | Aminisolicone SME253 | 0.30% | 120 | 122 | <10 |
| Comparative 3 | Silsoft A+ | 0.30% | 185 | 113 | <10 |
| Example | Emulsion E1 | 0.30% | >300 | 255 | 258 |

After 10 washes, in a pair comparison between the tress treated with Silsoft A+(comparative 3) and the tress treated with emulsion E1 (example), 9 subjects over 9 subjects assessed the conditioning of the tress treated with emulsion E1 was better than comparative 3 tress.

Ethnic Hair Straightening with Relaxer and Ironing

Ethnic Kinky hair were purchased from Hair International Inc. Hair sample was divided into 0.5 g hair strand. Each hair strand was relaxed with an hydroxide commercial hair straightening product from Softsheen-Carson (Optimum care, regular), following the recommended protocol. Hair was rinsed, shampooed with a neutralizer shampoo and dried with a blow drier. Hair was immersed in water or a 1% silicone dispersion obtained from emulsion E1 for 1 min and damp ironed for 7 min. 50 fibers were taken randomly for tensile testing for each samples. Data results in Table 6 showed that damp heat treatment without silicone (row #4) reduces break strength. Treatment with aminosilicone E1 helps reduce the strength loss (row #5).

TABLE 6

|  | Break strength (gmf/sq. micron) |
|---|---|
| Before relaxing | 0.0210 |
| After relaxing (no heat) | 0.0148 |
| Relaxing + heat + water | 0.0131 |
| Relaxing + heat + Emulsion E1 | 0.0153 |

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out the process of the invention but that the invention will include all embodiments falling within the scope of the appended claims.

The invention claimed is:

1. A method of treating thermally and/or chemically damaged hair comprising:
contacting hair which has been thermally and/or chemically damaged as a result of at least one of bleaching, dying, hair straightening, blow-drying and hair permanent treatments, the thermally and/or chemically damaged hair having at least one of a measured maximum width in the hair tip region (Lt) to the measured maximum width at the root end (Lr) ratio ((Lt)/(Lr)) of greater than about 3.7,
with a hair treating composition comprising an aminosilicone of the general formula (I):

$$MD_xD'_yM \qquad (I)$$

wherein:
$M=R^1R^2_2SiO_{1/2}$
$D=R^2_2SiO_{2/2}$, and
$D'=R^2R^3SiO_{2/2}$, and
where $R^1$ is an alkyl group having 12 to 50 carbon atoms, $R^2$ is a substituted or un-substituted hydrocarbon group having 1 to about 6 carbon atoms, $R^3$ is a 3-aminopropyl group and/or a N-(2-aminoethyl)-3-aminopropyl group, x has a value of 50 to about 1,500, and y has a value of 3.5 to about 40, wherein the hair treating composition is an aqueous composition which is an oil-in-water emulsion;
not rinsing the hair treating composition from the chemically and/or thermally damaged hair that has been treated with the hair treating composition; and,
applying heat for physically smoothing and/or shaping the treated hair;
the hair following such treatment having lower frizziness, the lower frizziness is a (Lt) to (Lr) ratio ((Lt)/(Lr)) of less than about 3.6.

2. The method of claim 1 wherein hair straightening comprises the treatment of the hair with an iron.

3. The method of claim 1 wherein $R^1$ is an alkyl group containing from about 15 to about 20 carbon atoms, $R^2$ is methyl and $R^3$ is a N-(2-aminoethyl)-3-aminopropyl group.

4. The method of claim 1 wherein $R^1$ is an alkyl group containing from about 30 to about 45 carbon atoms, $R^2$ is methyl and $R^3$ is a N-(2-aminoethyl)-3-aminopropyl group.

5. The method of claim 1 wherein the hair treating composition is at least one hair cosmetic.

6. The method of claim 1 wherein the thermally and/or chemically damaged hair is kinky hair.

7. The method of claim 1 wherein applying heat for physically smoothing and/or shaping the treated hair comprises use of at least one heat applying device selected from the group consisting of a straightening iron, a curling iron, a blow dryer, and a heating bonnet.

8. The method of claim 7 wherein the heat applying device is used in conjunction with at least one of a comb, brush, hair pin, hair clip, head band, and hair band.

9. A method of treating thermally and/or chemically damaged hair comprising:
contacting hair which has been thermally and/or chemically damaged as a result of at least one of bleaching, dying, hair straightening, blow-drying and hair permanent treatments, the thermally and/or chemically damaged hair having a measured maximum width in the hair tip region (Lt) to the measured maximum width at the root end (Lr) ratio ((Lt)/(Lr)) of greater than about 3.7, with a hair treating composition comprising an aminosilicone of the general formula (I):

$$MD_xD'_yM \qquad (I)$$

wherein:
$M=R^1R^2_2SiO_{1/2}$
$D=R^2_2SiO_{2/2}$, and
$D'=R^2R^3SiO_{2/2}$, and
where $R^1$ is an alkyl group having 16 to 18 carbon atoms, $R^2$ is methyl, $R^3$ is N-(2-aminoethyl)-3-aminopropyl, x has a value of 650, and y has a value of 3.5, wherein the hair treating composition is an aqueous composition which is an oil-in-water emulsion;
not rinsing the hair treating composition from the chemically and/or thermally damaged hair that has been treated with the hair treating composition; and,
applying heat for physically smoothing and/or shaping the treated hair;
the hair following such treatment having lower frizziness, and the lower frizziness is a (Lt) to (Lr) ratio ((Lt)/(Lr)) of less than about 3.6.

10. A method of treating thermally and/or chemically damaged hair comprising:
contacting hair which has been thermally and/or chemically damaged as a result of at least one of bleaching, dying, hair straightening, blow-drying and hair permanent treatment, the thermally and/or chemically damaged hair having at least one of a measured maximum width in the hair tip region (Lt) to the measured maximum width at the root end (Lr) ratio ((Lt)/(Lr)) of greater than about 3.7, with a hair treating composition comprising
a) an aminosilicone of the general formula (I):

$$MD_xD'_yM \qquad (I)$$

wherein:
$M=R^1R^2_2SiO_{1/2}$
$D=R^2_2SiO_{2/2}$, and
$D'=R^2R^3SiO_{2/2}$, and
where $R^1$ is an alkyl group having 12 to 50 carbon atoms, $R^2$ is a substituted or un-substituted hydrocarbon group having 1 to about 6 carbon atoms, $R^3$ is a 3-aminopropyl group and/or a N-(2-aminoethyl)-3-aminopropyl group, x has a value of 50 to about 1,500, and y has a value of 3.5 to about 40, and
b) one or more quaternary ammonium salts in an amount of from 0.1% to 5% by weight to the total weight of the composition.

* * * * *